US012751679B2

(12) United States Patent
Wang et al.

(10) Patent No.: US 12,751,679 B2
(45) Date of Patent: Oct. 6, 2026

(54) X-RAY IMAGING SYSTEM AND X-RAY IMAGING METHOD

(71) Applicant: GE Precision Healthcare LLC, Waukesha, WI (US)

(72) Inventors: Yan Wang, Beijing (CN); Zhaohua Guo, Beijing (CN); Aizhen Zhou, Beijing (CN); Ziyi Yuan, Beijing (CN); Chuanfu Zhang, Beijing (CN); Vishal Raghavan, Bengaluru (IN); Rakesh Bhat, Bengaluru (IN); Niketa Agarwal, Bengaluru (IN); Saurav Kumar, Bengaluru (IN); Raghuvaran Periaswamy, Bengaluru (IN)

(73) Assignee: GE Precision Healthcare LLC, Waukesha, WI (US)

( * ) Notice: Subject to any disclaimer, the term of this patent is extended or adjusted under 35 U.S.C. 154(b) by 141 days.

(21) Appl. No.: 18/769,656

(22) Filed: Jul. 11, 2024

(65) Prior Publication Data

US 2025/0017538 A1 Jan. 16, 2025

(30) Foreign Application Priority Data

Jul. 11, 2023 (CN) ......................... 202310847415.1

(51) Int. Cl.
*A61B 6/40* (2024.01)
*A61B 6/00* (2006.01)
*A61B 6/46* (2024.01)

(52) U.S. Cl.
CPC .......... *A61B 6/4035* (2013.01); *A61B 6/4452* (2013.01); *A61B 6/465* (2013.01); *A61B 6/469* (2013.01)

(58) Field of Classification Search
CPC ..... A61B 6/4035; A61B 6/4452; A61B 6/465; A61B 6/469
See application file for complete search history.

(56) References Cited

U.S. PATENT DOCUMENTS

| | | | | |
|---|---|---|---|---|
| 8,396,184 B2 * | 3/2013 | Shinno | ................. | A61B 6/4085 378/5 |
| 10,716,523 B2 | 7/2020 | Lee | | |
| 2013/0284939 A1 * | 10/2013 | DeMan | .................. | A61B 6/032 250/393 |

FOREIGN PATENT DOCUMENTS

| | | | | |
|---|---|---|---|---|
| CA | 3135998 A1 * | 10/2020 | ............. | G01S 15/08 |
| CN | 110870779 A | 3/2020 | | |

* cited by examiner

*Primary Examiner* — Uzma Alam
*Assistant Examiner* — Fani Polyzos Boosalis

(57) ABSTRACT

The X-ray imaging system includes a camera unit, a display unit, an input unit, an exposure assembly, and a control unit. The camera unit is configured to acquire a real-time optical image of a subject under examination. The display unit is configured to display the real-time optical image. The input unit is configured to receive a user operation and to form a target region on the user interface by changing the position of a center of the collimation region. The exposure assembly includes an X-ray source, a detector, and a collimator, the collimator having an opening configured to display a collimation region on the subject under examination. The control unit is configured to control movement of the X-ray source and the detector to align with the center of the target region, and control the opening of the collimator such that the collimation region is aligned with the target region.

14 Claims, 10 Drawing Sheets

X-RAY IMAGING SYSTEM AND X-RAY IMAGING METHOD

CROSS-REFERENCE TO RELATED APPLICATIONS

This application is based on and claims priority to Chinese Patent Application No. 202310847415.1, filed on Jul. 11, 2023, the entire contents of which is herein incorporated by reference.

TECHNICAL FIELD

The present invention relates to medical imaging technologies, and specifically to an X-ray imaging system and an X-ray imaging method.

BACKGROUND

In an X-ray imaging system, radiation from an X-ray source is emitted toward a subject, and the subject under examination is usually a patient in a medical diagnosis application. Some of the radiation passes through the subject under examination and impacts a detector, which is divided into a matrix of discrete elements (e.g., pixels). The detector elements are read to generate an output signal based on the amount or intensity of radiation that impacts each pixel region. The signal can then be processed to generate a medical image that can be displayed for review, and the medical image can be displayed in a display apparatus of the X-ray imaging system.

Usually, the subject under examination enters a scan room, and a user needs to assist in placement or positioning in the scan room, for example, adjusting the position of the X-ray source and detector, informing the subject under examination of the required body position or posture, etc. In addition, the user also needs to manually adjust the collimator so that the collimation region can be aligned with a region of interest of the subject under examination. Then the user needs to enter the control room for exposure control and image processing, and for the next subject under examination, the above steps need to be repeated, which is cumbersome and inefficient, and the manual adjustment of the collimator is also time-consuming and imprecise. For example, if the subject under examination moves, the user needs to return to the scan room to carry out adjustments.

SUMMARY

Provided in the present invention are an X-ray imaging system and an X-ray imaging method.

Exemplary embodiments of the present invention provide an X-ray imaging system including an exposure assembly including an X-ray source, a detector, and a collimator, the collimator having an opening for controlling a collimation region, a camera unit aligned with the detector for acquiring a real-time optical image of a subject under examination, the real-time optical image including a center of the collimation region, a display unit operably connected to the camera unit, the display unit including a user interface configured to display the real-time optical image, an input unit operably connected to the display unit, the input unit configured to receive an operation of a user and form a target region on the user interface by changing a position of the center of the collimation region or re-framing a region of the collimation region, and a control unit operably connected to the exposure assembly, the control unit configured to control, based on the target region, automatic movement of the X-ray source and the detector to align with a center of the target region, and control the opening of the collimator such that the collimation region is aligned with the target region.

Exemplary embodiments of the present invention further provide an X-ray imaging method, the method includes acquiring and displaying a real-time optical image of a subject under examination, the real-time optical image including an initial collimation region and a center of the collimation region. The method also includes controlling, based on a target region obtained by changing a position of the center of the collimation region or re-framing, an X-ray source and a detector to automatically move to be aligned with the center of the target region, and controlling an opening of a collimator such that the collimation region is aligned with the target region.

Other features and aspects will become apparent from the following detailed description, drawings, and claims.

BRIEF DESCRIPTION OF THE DRAWINGS

The present invention can be better understood by means of the description of the exemplary embodiments of the present invention in conjunction with the drawings, in which.

DETAILED DESCRIPTION

Figure 1:
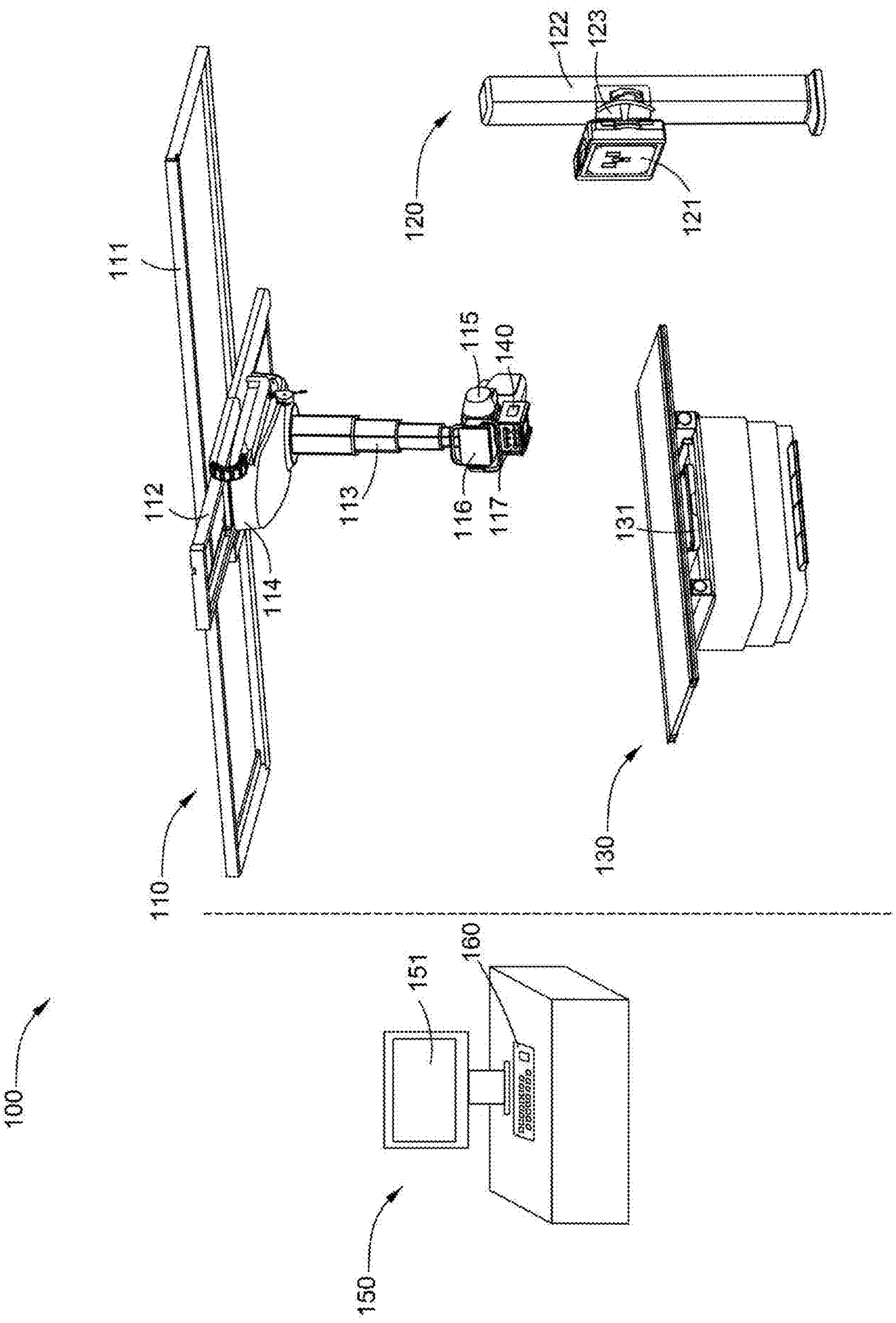
FIG. 1 is a schematic diagram of an X-ray imaging system according to some embodiments of the present invention.

Specific embodiments of the present invention will be described below. It should be noted that in the specific description of said embodiments, for the sake of brevity and conciseness, the present description cannot describe all of the features of the actual embodiments in detail. It should be understood that in the actual implementation process of any embodiment, just as in the process of any one engineering project or design project, a variety of specific decisions are often made to achieve specific goals of the developer and to meet system-related or business-related constraints, which may also vary from one embodiment to another. Furthermore, it should also be understood that although efforts made in such development processes may be complex and tedious, for a person of ordinary skill in the art related to the content disclosed in the present invention, some design, manufacture, or production changes made based on the technical content disclosed in the present disclosure are common technical means, and should not be construed as the content of the present disclosure being insufficient.

Unless defined otherwise, technical terms or scientific terms used in the claims and description should have the usual meanings that are understood by those of ordinary skill in the technical field to which the present invention belongs. The terms "first" and "second" and similar terms used in the description and claims of the patent application of the present invention do not denote any order, quantity, or importance, but are merely intended to distinguish between different constituents. The terms "one" or "a/an" and similar terms do not express a limitation of quantity, but rather that at least one is present. The terms "include" or "comprise" and similar words indicate that an element or object preceding the terms "include" or "comprise" encompasses elements or objects and equivalent elements thereof listed after the terms "include" or "comprise", and do not exclude other elements or objects. The terms "connect" or "link" and similar words are not limited to physical or mechanical connections, and are not limited to direct or indirect connections.

In the present invention, the "collimation region" refers to the size of an opening of a collimator, i.e., the irradiation range of X-rays. The "target region" is a region irradiated by X-rays, which is operated, or decided, or determined by a user, wherein the purpose of the target region is to confirm the position and size of the collimation region which is to be adjusted to align or overlap with the target region. The "reference region" refers to a reference range of a target region correspondingly formed with a current position of a mouse as a temporary end point after the user enters a starting point during a process of re-framing the target region, and when the position of the end point is determined, the reference region is the target region. The "detector plane" is a plane on which a detector surface is located, and the "target region plane" is a plane on which an optical image is located.

Figure 2:
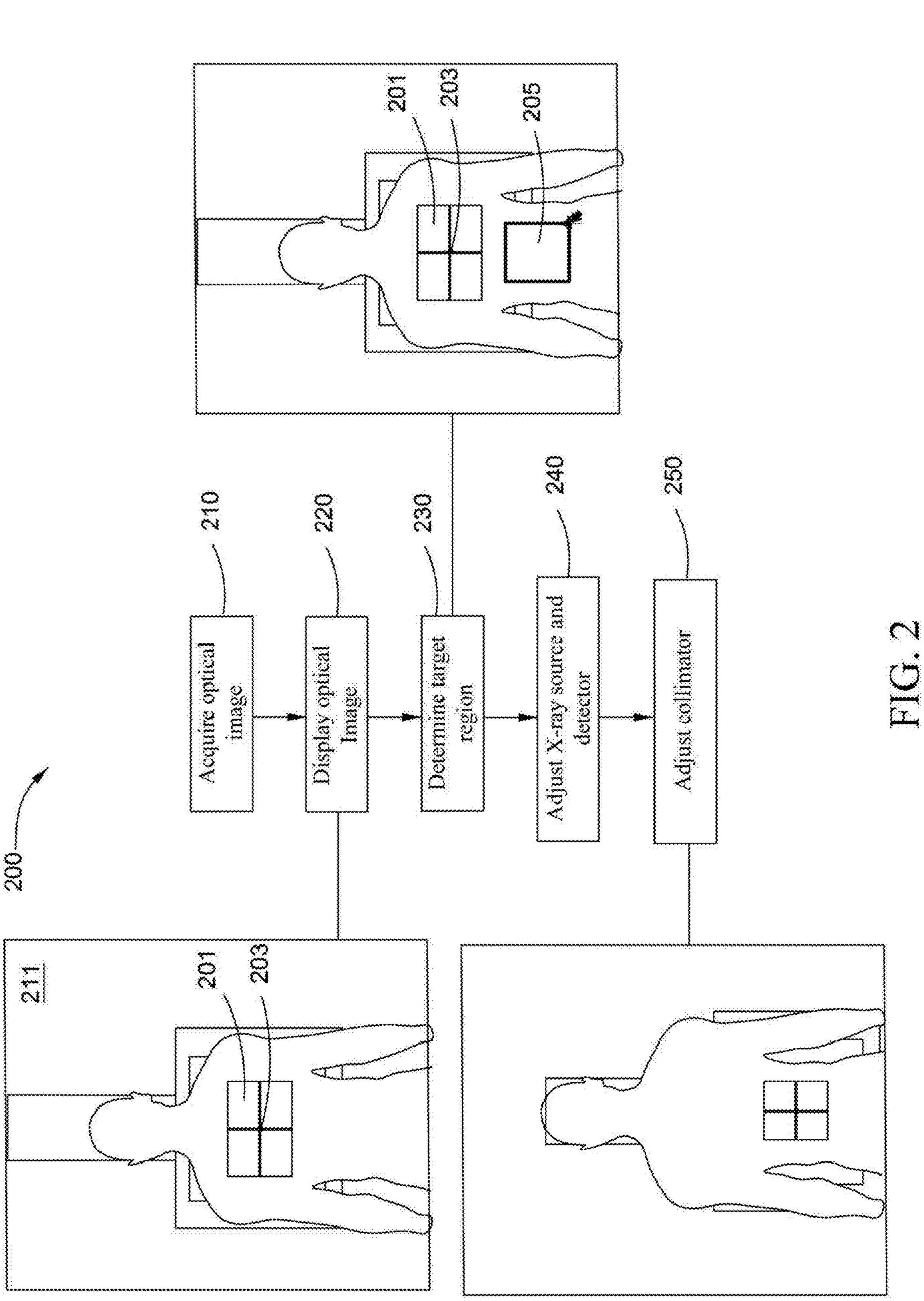
FIG. 2 is a schematic diagram of a control logic of a control unit in an X-ray imaging system according to some embodiments of the present invention.

FIG. 1 illustrates an X-ray imaging system 100 according to some embodiments of the present invention, and FIG. 2 illustrates a schematic view of a collimator of the X-ray imaging system as shown in FIG. 1. As shown in FIG. 1, the X-ray imaging system 100 includes a suspension apparatus 110, a wall stand apparatus 120, and an examination table apparatus 130. The suspension apparatus 110 includes a longitudinal guide rail 111, a transverse guide rail 112, a telescopic cylinder 113, a sliding member 114, a tube assembly 115, and a tube control apparatus 116.

For case of description, in the present invention, the x-axis, y-axis, and z-axis are defined as the x-axis and y-axis being located in the horizontal plane and perpendicular to one another, and z-axis being perpendicular to the horizontal plane. Specifically, the direction in which the longitudinal guide rail 111 is located is defined as the x-axis, the direction in which the transverse guide rail 112 is located is defined as the y-axis direction, and the direction of extension of the telescopic cylinder 113 is defined as the z-axis direction, and the z-axis direction is the vertical direction.

The longitudinal guide rail 111 and the transverse guide rail 112 are perpendicularly arranged, the longitudinal guide rail 111 being mounted on a ceiling and the transverse guide rail 112 being mounted on the longitudinal guide rail 111. The telescopic cylinder 113 is configured to carry the tube assembly 115.

The sliding member 114 is provided between the transverse guide rail 112 and the telescopic cylinder 113. The sliding member 114 may include components such as a rotating shaft, a motor, and a reel. The motor can drive the reel to rotate around the rotating shaft, which in turn drives the telescopic cylinder 113 to move along the z-axis and/or slide relative to the transverse guide rail. The sliding member 114 is capable of sliding relative to the transverse guide rail 112, i.e., the sliding member 114 is capable of driving the telescopic cylinder 113 and/or the tube assembly 115 to move in the y-axis direction. Further, the transverse guide rail 112 can slide relative to the longitudinal guide rail 111, which in turn drives the telescopic cylinder 113 and/or the tube assembly 115 to move in the x-axis direction.

The telescopic cylinder 113 includes a plurality of cylinders having different inner diameters, and the plurality of cylinders can be sleeved, sequentially from bottom to top, in the cylinder located thereabove, thereby achieving telescoping, and the telescopic cylinder 113 can be telescopic (or movable) in the vertical direction, i.e., the telescopic cylinder 113 can drive the tube assembly 115 to move along the z-axis direction. The lower end of the telescopic cylinder 113 is further provided with a rotating part, and the rotating part can drive the tube assembly 115 to rotate.

The tube control apparatus (console) 116 is mounted on the tube assembly 115. The tube control apparatus 116 includes user interfaces such as a display screen and a control button so as to be configured to perform pre-capturing preparations, such as patient selection, protocol selection, positioning, etc.

The movement of the suspension apparatus 110 includes the movement of the tube assembly along the x-axis, y-axis, and z-axis, as well as the rotation of the tube assembly in the horizontal plane (the axis of rotation is parallel to or overlaps with the z-axis) and in the vertical plane (the axis of rotation is parallel to the y-axis). In the above motion, a motor is usually used to drive a rotating shaft which in turn drives corresponding components to rotate in order to achieve the corresponding movement or rotation, and the corresponding control components are generally mounted in the sliding member 114. The X-ray imaging system further includes a motion control unit (not shown in the figures) that is capable of controlling the movement of the suspension apparatus 110, and furthermore, the motion control unit is capable of receiving a control signal to control the corresponding component to move accordingly to drive the arena assembly to reach a preset or specified position.

The wall stand apparatus 120 includes a first detector 121, a wall stand 122, and a connecting member 123. The connection member 123 includes a support arm that is vertically connected in the height direction of the wall stand 122 and a rotating bracket that is mounted on the support arm, and the first detector 121 is mounted on the rotating bracket. The wall stand apparatus 120 further includes a detector driving apparatus that is arranged between the rotating bracket and the first detector 121, which is driven by the detector driving apparatus to move in a direction parallel to the height direction of the wall stand 122 in the plane held by the rotating bracket, and the first detector 121 can further be rotated relative to the support arm to form an angle with the wall stand. The first detector 121 has a plate-like structure whose orientation is variable so that the X-ray incident surface can become vertical or horizontal depending on the incident direction of the X-rays.

A second detector 131 is included on the examination table apparatus 130, and the selection or use of the first detector 121 and the second detector 131 may be determined based on a capture site of patient and/or a capture protocol, or may be determined based on the position of the subject under examination that is obtained from a camera capture, so as to conduct a supine, prone or standing capture examination. FIG. 1 shows an example diagram of a wall stand and an examination table, and it should be understood by those skilled in the art that wall stands and/or examination tables of any form or arrangement can be selected, or only the wall stand can be mounted, and the wall stand and/or examination table is not intended to limit the overall solution of the present application.

The X-ray imaging system 100 of the present invention further includes an exposure assembly, the exposure assembly including an X-ray source, a collimator 117, and the detector 121/131. Specifically, the X-ray source is provided within the tube assembly 115 and the collimator 117 is typically mounted below the X-ray source.

The collimator 117 includes four movable collimator shutters, the four collimator shutters being a material capable of absorbing X-rays, and the four collimator shutters together enclose to form a square or rectangle, and, after enclosing, the four collimator shutters also form an opening in the middle. The opening is the collimator opening, and the size of the collimator 117 opening determines the X-ray irradiation range, i.e., the size of the exposure field of view (FOV). X-rays can pass through the opening of the collimator to a region of interest (ROI) of the subject under examination, and other X-rays are absorbed by the shutters to prevent the subject under examination from absorbing an excess unnecessary dose. The position of the X-ray source and collimator 117 in the transverse direction determines the position of the exposure field of view (FOV) on the subject under examination.

In some embodiments, the collimator includes a drive unit that controls or drives the movement of the collimator shutters, the drive unit being able to control each collimator shutter separately, i.e., the four shutters in the collimator can be controlled to move separately or individually, so as to control or adjust the size of the opening. For example, when a large opening of the collimator is required, the drive unit is able to drive at least one of the four shutters in a direction away from the opening, and when a small opening of the collimator is required, the drive unit is able to drive at least one of the four shutters in a direction closer to the opening. During the process of adjusting the size of the opening, it is possible to move only one of the shutters, or two shutters that are arranged opposite to one another, or all four shutters at the same time, depending on the size of the collimation region required.

Typically, the exposure assembly may include at least one of the first detector 121 that is provided in the wall stand apparatus 120 and the second detector 131 that is in the examination table apparatus 130, wherein at least a portion of the X-rays can be attenuated by means of the patient and can be incident on the detector 121/131.

During the imaging process, the center of the X-ray source, i.e., the central ray of the X-ray beam, often needs to be aligned with the center of the detector. In some embodiments, the X-ray source and the detector can be controlled in a linked manner, for example, the position and angle of the X-ray source can be controlled by controlling the movement of the suspension apparatus, and then, by means of monitoring information of the X-ray source that is provided on the detector, the detector can be automatically moved or rotated to a position that is aligned with the X-ray source, i.e., a linked control of the two can be achieved. Vice versa, the detector can be controlled to move or rotate and then the X-ray source can be automatically moved or rotated, based on monitoring information provided on the X-ray source, to a position that aligns with the detector.

In some embodiments, the X-ray imaging system 100 further includes a camera unit 140, and the camera unit 140 is aligned with the detector so as to be configured to acquire a real-time optical image of the subject under examination. In addition, the camera is able to acquire an image of the detector, etc.

Specifically, the camera unit 140 is mounted on the suspension apparatus 110, and further, on the side of the collimator 117. The camera unit may include one or more cameras, for example, a digital camera, an analog camera, etc., or a depth camera, an infrared camera, or an ultraviolet camera, etc., or a 3D camera, a 3D scanner, etc., or a red, green, and blue (RGB) sensor, an RGB depth (RGB-D) sensor, or other devices that can capture color image data of a target subject. In some embodiments, the camera unit 140 is further provided with a control module that can control the rotation of the camera unit to adjust the capture range of the camera unit. In other embodiments, the camera unit is a panoramic camera that can take an image of the entire body of the subject under examination.

The camera unit 140 can acquire depth information or a depth image of the subject under examination. Typically, the depth information is calculated from a 3D point cloud that is acquired by the camera. In addition, the real-time optical image can be used to acquire at least one of the thickness, height, position, body position, pose, etc. of the subject under examination.

In some embodiments, the camera unit 140 may also be a camera unit that is mounted in a fixed position, or fixed in any other way in the scan room.

In some embodiments, the optical image acquired by the camera unit is not limited to a single optical image, but may also include a dynamic real-time video stream, i.e., a series of real-time optical images. The real-time optical image together with at least one indicator may be presented continuously and in real-time on a display unit, and the at least one indicator may include an initial collimation region and the center of the collimation region.

The X-ray imaging system 100 further includes a display unit 150, the display unit 150 being operably connected to the camera unit, the display unit 150 including a user interface 151, the user interface 151 being configured to display the real-time optical image, and the real-time optical image further including at least one indicator thereon, for example, the initial collimation region and the center of the collimation region. Of course, the at least one indicator may also include a calibration line of the collimator, etc. Specifically, the image range of the real-time optical image displayed on the user interface can be adjusted, for example, by zooming in, zooming out, moving the viewing range, etc.

Figure 3:
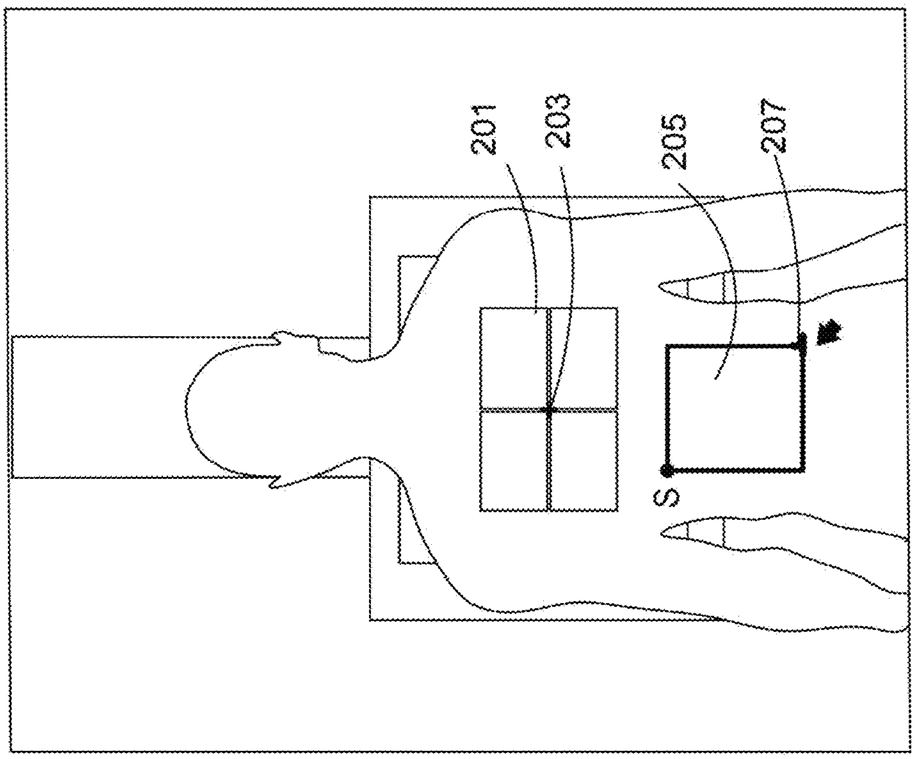
FIG. 3 is a schematic diagram of a first embodiment for determining a target region according to FIG. 2.

Specifically, the display unit 150 can include any form of display screen, which may be a main display screen that is located in the control room, a display screen of the tube control apparatus 116 that is located in the scan room, or a mobile display, such as a tablet, a cell phone, etc. The user interface 151 in FIG. 3 illustrates a real-time optical image of the subject under examination. However, it should be understood by those of ordinary skill in the art that the user interface 151 is also capable of being configured to display one or more items with respect to the information about the subject under examination, the display and options of scanning protocols, positioning images, medical images, image post-processing parameters, etc.

The X-ray imaging system further includes an input unit 160, configured to receive a user operation. The input unit 160 can include an input device such as a touchscreen, a keyboard, a mouse, a voice-activated control unit, or any other suitable input device, and a user can input an operation signal/control signal into the control unit by means of the input unit 160.

The X-ray imaging system 100 further includes a control unit (not shown in the figures), which may be a main control unit that is located in the control room, a tube control unit that is mounted on the suspension apparatus, a mobile or portable control unit, or any combination of the above. The control unit may include a source control unit and a detector control unit. The source control unit is configured to command the X-ray source to emit X-rays for image exposure. The detector control unit is configured to select an appropriate detector from among a plurality of detectors and to coordinate the control of various detector functions, such as automatically selecting a corresponding detector according to the position or pose of the subject under examination, or may perform various signal processing and filtering functions, and specifically for the initial adjustment of the dynamic range, interleaving of digital image data, etc. In some embodiments, the control unit may provide power and timing signals for controlling the operation of the X-ray source and the detector.

In some embodiments, the control unit may also be configured to use a digitized signal to reconstruct one or more required images and/or determine useful diagnostic information corresponding to the patient, wherein the control unit may include one or more dedicated processors, graphics processing units, digital signal processors, microcomputers, microcontrollers, application-specific integrated circuits (ASICs), field-programmable gate arrays (FPGAs), or other appropriate processing apparatuses.

Of course, the X-ray imaging system may also include other numbers or configurations or forms of control units, for example, the control unit may be local (e.g., co-located with one or more X-ray imaging systems 100, e.g., within the same facility and/or the same local network). In other implementations, the control unit may be remote and thus accessible by means of a remote connection (for example, by means of the Internet or other available remote access technologies). In a specific implementation, the control unit may also be configured in a manner similar to the configuration of cloud technology, and may be accessed and/or used in a manner substantially similar to the manner of accessing and using other cloud-based systems.

FIG. 2 illustrates a schematic diagram of a control logic 200 of the control unit of some embodiments of the present invention. As shown in FIG. 2, firstly, the control unit can be operably connected to the camera unit and the display unit, and the control unit can control the camera unit (component 140 as shown in FIG. 1) to acquire (210) a real-time optical image 211 of the subject under examination. The control unit is able to control the transfer of the real-time optical image between the camera unit and the display unit, and to display (220) the real-time optical image 211 on the user interface of the display unit. The optical image 211 further includes an indicator of the collimation region 201 and the center 203 of the collimation region, in addition to the images of the subject under examination and the detector.

The collimation region refers to a region corresponding to the surface of the subject under examination that is irradiated by the X-rays through the opening of the collimator. The collimation region in the optical image is not acquired by actual irradiation of the X-rays, but by the irradiation of a light source that is built into the collimator 117, which is used to show the user the current size of the collimation region. In some embodiments, the optical image also includes a center line (not shown in the figure) acquired by laser irradiation, which can be a straight line through the center point or cross lines through the center point. The center of the collimation region can be directly configured in the collimator, so as to be shown on the optical image while the light source is illuminated, or can be acquired by simultaneously calculating and automatically marking on the optical image at a later stage while the optical image is shown, and there is no restriction on how the center can be shown.

Secondly, the control unit is connected to the input unit (component 160 shown in FIG. 1) to receive an operation from the user to form 230 a new target region 205 by changing the position of the center of the collimation region or re-framing a region on the user interface. Next, the control unit is operably connected to the exposure assembly and is configured to control 240, based on the target region 205, the automatic movement of the X-ray source and the detector to align with the center of the target region 205, and to control 250 the opening of the collimator such that the collimation region is aligned with the target region 205, i.e., the collimation region reaches the current position of the target region 205. That is, the collimation region overlaps with the target region 205.

Specifically, the control unit is able to acquire an initial region of interest of the subject under examination based on the information of the subject under examination, for example, the age, the capture region, the possible type of disease of the subject under examination, etc., and initially configure the exposure assembly to align with the initial region of interest, and form an initial collimation region on the body surface of the subject under examination based on the light source that is arranged in the collimator, and the collimation region can be observed through the real-time optical image acquired by the camera, and then the user is able to determine whether the collimation region is accurate based on the information of the subject under examination or other information.

FIG. 3 illustrates a schematic diagram of a first embodiment for determining a target region according to FIG. 2. As shown in FIG. 3, when the user finds that the size of the collimation region 201 or the location of a point of the center 203 is not accurate, the user can acquire the target region 205 by re-framing a region, i.e., the user can "draw" a target region frame on the user interface by means of an input unit such as a mouse, a keyboard, or a touchscreen to acquire a new target region. Preferably, the user can operate within the range of the real-time optical image on the user interface via the input unit to re-frame the target region.

In some aspects of the embodiment, the control unit can, after receiving a valid starting point S input, calculate, based on the movement of the input unit (e.g., a mouse), a real-time reference region and display the same on the display unit, and after receiving a valid end point input, acquire the target region.

Specifically, the control unit is configured to receive a first press position S inputted by the input unit (e.g., a mouse) and determine the first press position S as a valid starting point when the first press position S is within the range of the optical image, and of course, it can also be configured as such that when the first press position is within the outline range of the subject under examination, the first press position is determined as a valid starting point. Alternatively, it can also be configured as such that when the first press position is within a preset distance from the outline boundary of the subject under examination, the first press position is determined as a valid starting point.

During the process of receiving a valid starting point but not yet receiving an end point, as the input unit (e.g., a mouse) moves, the current dwell position of the mouse is defined as a temporary end point, and the control unit is able to calculate and display on the user interface (or within the range of the optical image) a reference region formed by the starting point and the temporary end point to indicate to the user on the user interface the possible range of the target region, and the range of the reference region can be finally confirmed when confirmation of the end point is received, i.e., when the end point is received, the reference region is the target region.

To make it easier to show the position of the end point, the temporary end point is further displayed, or highlighted, or indicated by an indicator 207 during mouse movement, for example, by a "cross", or "L", or "inverted T" symbol to show the position of the temporary end point.

In some embodiments, the input unit is a mouse, and the current position of the mouse can be displayed in real-time on the user interface as the user re-frames the target region.

For the confirmation of the end point, in one aspect of the embodiment, the control unit is able to re-frame the target region using two mouse clicks to select the starting point and the end point, respectively. Specifically, the control unit is configured to receive a second press position inputted by the input unit and to determine the second press position as a valid end point when the second press position has a preset distance from the first press position. Specifically, the control unit is able to determine that the second press position is a valid end point when the second press position does not overlap with the first press position, and, of course, the control unit is also able to determine that the second press position is a valid end point when the second press position is to the lower right of the first press position, which is configurable and selectable.

Of course, in another aspect of the embodiment, the control unit can re-frame the target region by pressing and moving the mouse and taking as the end point is the position at which the mouse is released, i.e., clicking the mouse to determine the starting point, and then moving the mouse while holding the mouse click, and then releasing the mouse to determine the end point, thereby forming the target region. Specifically, the control unit can also be configured to receive a first release position inputted by the input unit and determine the first release position as a valid end point when the first release position has a preset distance from the first press position. Of course, the control unit can determine that the first release position is a valid end point when the first release position does not overlap with the first press position, and of course, the control unit can also determine that the first release position is a valid end point when the first release position is to the lower right of the first press position, which is configurable and selectable.

In some non-limiting embodiments, the position of the starting point can be configured to be a terminal point within the target region, or can be configured to be the center point of the target region. For example, the user selects the first press position as the center of the target region, and then determines the desired target region through a reference region frame that is shown during the mouse movement, and then determines the position of the end point.

When the user determines the starting point (the first press position) and, during the process of moving the mouse, finds that the current target region is not accurate, the user can also cancel the selection of the current starting point by means of double-clicking the mouse or a shortcut key on the keyboard, etc., and select the starting point again.

In some aspects of the embodiment, the input unit is a touchscreen, and the control unit is able to, after receiving a valid starting point input, calculate, based on the movement of a finger, a real-time reference region and display the same on the display unit, and after receiving a valid end point input, acquire a target region, the specific settings thereof being the same as the settings of the mouse, which will not be repeated herein.

Although two methods of re-framing the target region are described above, it should be understood by those skilled in the art that the target region can also be framed with any other operational methods.

Figure 4:
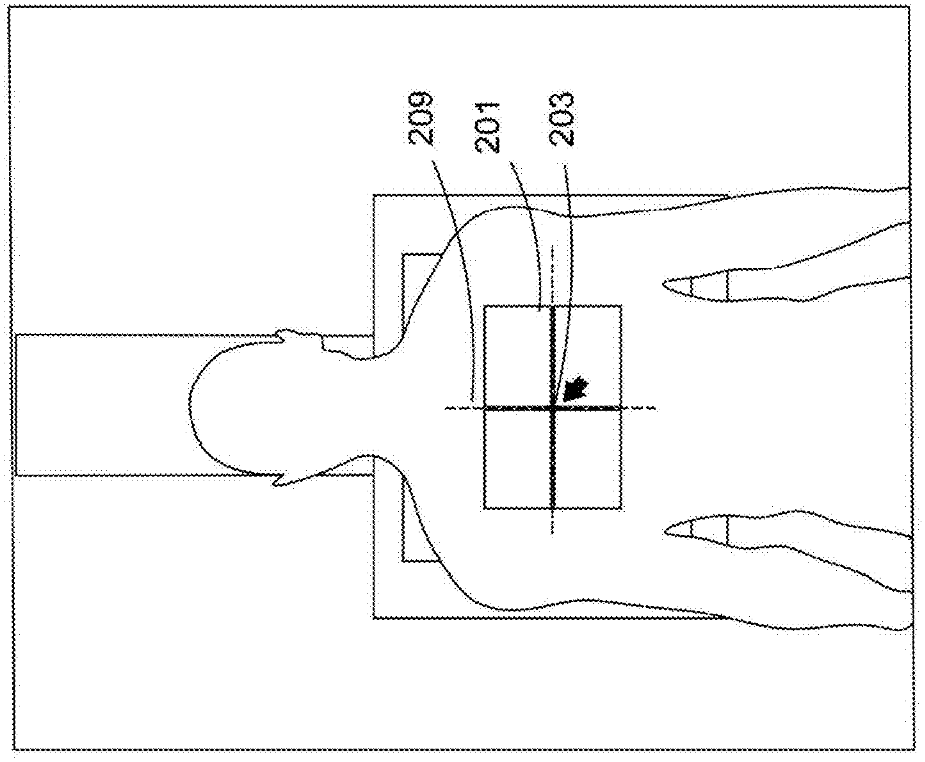
FIG. 4 is a schematic diagram of a second embodiment for determining a target region according to FIG. 2.

FIG. 4 illustrates a schematic diagram of a second embodiment for determining a target region according to FIG. 2. As shown in FIG. 2, when the user finds that the size or dimensions of the collimation region are correct, i.e., the user does not want to change the size of the collimation region, but the center position of the collimation region is inaccurate, the user can acquire the target region by directly changing the position of the center 203 of the collimation region, and the exposure assembly is accordingly moved to a position that is aligned with the target region. Specifically, the changing the position of the center of the collimation region includes translating the center of the collimation region or reselecting the center of a new collimation region.

Specifically, the user chooses or selects the center 203 of the collimation region by means of the input unit, and the control unit is able to further control the display of a moving reference line 209 on the user interface (or within the range of the optical image) based on the operation received by the input unit so as to indicate a reference position in which the user can move in at least one direction, such as up, down, left, or right.

The translation method may include, but is not limited to: clicking and dragging, selecting and then adjusting the direction up, down, left, and right by means of a keyboard shortcut key, or directly performing translation by means of the operation buttons arranged on the user interface, voice control, or other means, and the translation method can be operated by means of a mouse, a keyboard, or by operating the touchscreen, or directly by means of voice control.

Specifically, the reselecting includes performing selecting or clicking at an arbitrary position on the user interface, and the position becomes the center of the new target region, but the size of the target region does not change.

In some embodiments, the user can perform an operation directly on the user interface to form a new target region. In some other embodiments, the user interface can also be provided with one or more options or buttons or a toggle button corresponding to the operation of changing (translating or reselecting) the position of the center of the collimation region and the operation of re-framing.

In some embodiments, when the control unit receives the end point position inputted by the input unit, the target region is also determined, and the control unit can then control the exposure assembly to move or adjust to align with the target region. For example, while the mouse button is released, the suspension apparatus and the wall stand apparatus move simultaneously and the collimator shutters are controlled to move to adjust the opening range.

In other embodiments, a target region confirmation option may also be configured on the user interface of the display unit for confirming the range of the target region. Specifically, the confirmation option may be configured on the optical image or may be configured at any suitable position outside the range of the optical image on the user interface. When the user determines the framed target region, and confirms the current target region by the operation of the confirmation option, the exposure assembly automatically moves to a position that is aligned with the target region, thereby effectively avoiding confusion or misoperation etc. caused by repetitive operations, especially when two presses are used to determine the target region.

While the above illustrates both changing the position of the center of the collimation region and re-framing the target region, it should be understood by those of skill in the art that the size or position of the collimation region can be changed in any other suitable manner, e.g., by manipulating the collimation region directly on the user interface, including selecting and dragging either border of the collimation region, or dragging any terminal point of the collimation region, etc.

In some embodiments, the control unit is able to calculate the position or coordinates of the center of the target region, then determine the length and width of the target region based on the position or coordinates of the center, and move the X-ray source and detector to align with the center of the target region based on the position of the center, and adjust the opening of the collimator based on the length and width. Specifically, once the starting point and the end point of the target region are determined, the position of the center point can be acquired, and according to the distance between the center point and the end point, the coordinate position of the end point relative to the center point can be acquired. That is, the distance between the center point and two edges that together form the end point can also be acquired, which are the length and width of the target region. Specifically, relative coordinate positions can be acquired based on the coordinates of the starting point and the end point, i.e., the center point, and the length and width of the target region can be confirmed, and then the exposure assembly can be adjusted accordingly.

In some embodiments, when the subject under examination is lying on an examination table, a detector located on a lower side of a table panel can move to be aligned with the center of the target region. Specifically, the center of the detector is aligned with the center of the target region. In some embodiments, when the range of the target region exceeds the maximum limit of the range of movement of the detector, the control unit can automatically control or reduce the target region such that the target region can be located within the range of the detector. Specifically, when the detector has moved to a certain corner of the table, the range of the detector in this case is the size of a detector panel. If the target region in this case exceeds the range of the detector in a direction away from the table panel, the control unit can automatically reduce the target region to match the range of the detector.

In another embodiment, when the subject under examination stands in front of the wall stand apparatus, the height of the detector located on the wall stand apparatus is adjustable, but the horizontal position thereof is not adjustable. The control unit can control the detector to move to be aligned with the center of the target region, but in the horizontal direction, it is possible that the center of the detector cannot be aligned with the center of the target region. In this case, exposure can still be performed without adjusting the position or size of the target region as long as the target region is within the range of the detector.

In some embodiments, the real-time reference region shown during a process when the user re-frames the target region may be a rectangle as shown in FIG. 2. In another embodiment, the real-time reference region shown during a process when the user re-frames the target region can be a non-rectangular real-time boundary, and by displaying the real-time boundary, the user can be given the most accurate range of the target region.

Figure 5:
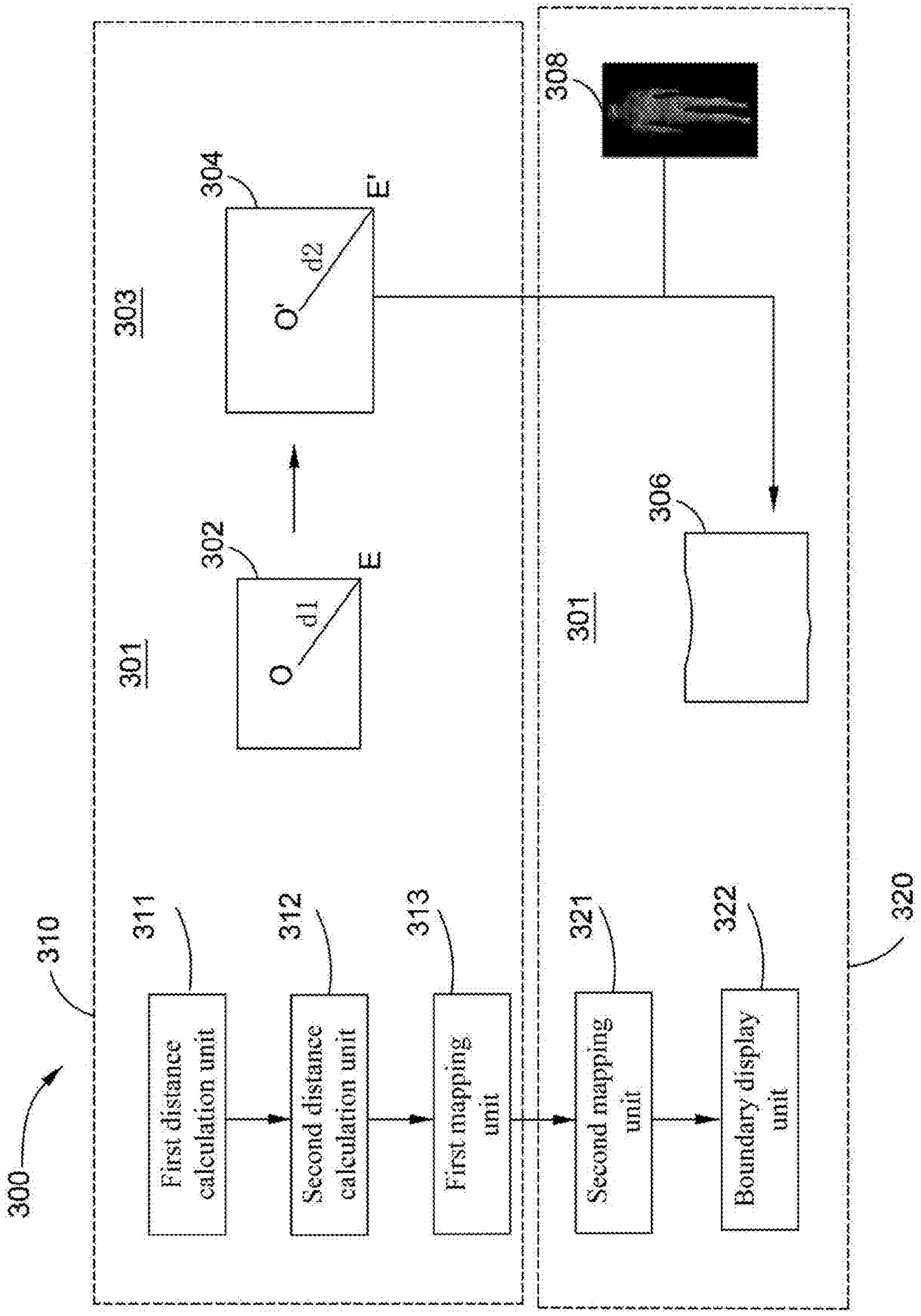
FIG. 5 is a schematic diagram of a control logic of a control unit in an X-ray imaging system according to some embodiments of the present invention.

FIG. 5 illustrates a schematic diagram of a control logic 300 of a control unit in an X-ray imaging system according to some embodiments of the present invention. FIG. 5 illustrates the control logic that is capable of displaying the current real-time boundary during a process when the user selects or determines a target region. Specifically, when the control unit receives a valid starting point position, during the mouse movement, the control unit is able to calculate, according to the control logic shown in FIG. 5, the real-time boundary corresponding to the reference region and display the same. The reference region is a target region formed by the temporary end point corresponding to the current mouse position, and the real-time boundary is usually an irregular shape, which is related to the thickness of the subject under examination.

Specifically, the control unit includes a first unit 310 and a second unit 320. The first unit 310 is configured to acquire a mapping region corresponding to the reference region mapped to the detector plane, and the second unit 320 is configured to calculate, based on the size of the mapping region and the thickness information of the subject under examination, the real-time boundary of the reference region and display the same.

Specifically, the first unit 310 includes a first distance calculation unit 311, a second distance calculation unit 312, and a first mapping unit 313. The first distance calculation unit 311 is able to calculate a first distance d1 between the center O of a reference region 302 and a temporary end point E of the reference region 302. The second distance calculation unit 312 is able to calculate a second distance d2 corresponding to the first distance d1 relative to a detector plane 303 based on the thickness information of the subject under examination at the temporary end point E and the distance SID between the ray source and the detector, and the first mapping unit 313 determines the mapping region 304 based on the second distance d2.

Specifically, the first distance calculation unit 311 is able to acquire the first distance d1 between the center O of the reference region 302 and the temporary end point E of the reference region 302 based on the confirmed starting point from the input unit and the position of the temporary end point captured from the mouse dwell position.

Figure 6:
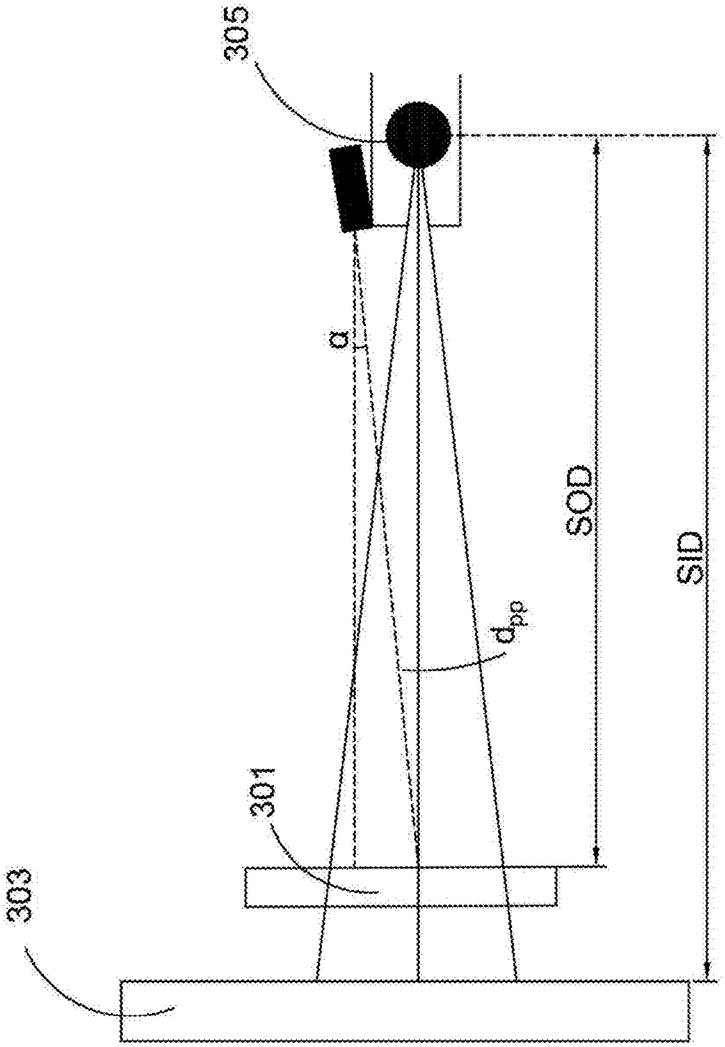
FIG. 6 is a schematic diagram of a second distance calculation unit according to FIG. 5.

FIG. 6 illustrates a schematic diagram of a second distance calculation unit as described in FIG. 5. For case of description, the plane in which the detector surface is located is defined as the detector plane 303 and the plane in which the optical image is located is defined as the target region plane 301 in the present invention. The camera unit is mounted on the side of the collimator, so that in order to enable the camera unit to be capable of being aligned with the center of the detector, the camera unit is fixed on the side of the collimator at a preset angle. Therefore, a fixed first angle α is present between the camera unit and the side of the collimator. A second calculation unit is configured to acquire, based on the first angle and thickness information of the subject under examination, the distance SOD between the X-ray source and the subject under examination, and calculate, based on the ratio between the distance SOD and the distance SID, the second distance corresponding to the first distance relative to the detector plane. As shown in FIG. 6, since the distance SID from the X-ray source 305 to the detector plane 303 is known to the system, the distance SOD between the X-ray source 305 and the subject under examination can be obtained by calculating according to the thickness information dppcos(α) of the subject under examination at the position of the temporary end point corresponding to the current reference region and the first angle α, and then according to SOD and SID, the second distance d2 in the detector plane 303 corresponding to the first distance d1 in the target region plane 301 can be accordingly calculated and obtained. The second distance d2 is the distance between a mapping center point O' and a mapping end point E' in the detector plane 303.

The first mapping unit 313 is able to acquire, based on the second distance d2, the corresponding mapping region 304 after the reference region is mapped to the detector plane.

Referring further to FIG. 5, the second unit 320 includes a second mapping unit 321 and a boundary display unit 322. The second mapping unit 321 can acquire, based on the thickness corresponding to a plurality of points on the boundary of the mapping region 304, the corresponding position coordinates of the plurality of points on the target region plane, and the boundary display unit 322 can display the real-time boundary based on the position coordinates of the plurality of points.

The second mapping unit 321 can select the coordinate positions of a plurality of points on the border of the mapping region 304, and acquire the corresponding coordinate positions on the target region plane based on the thickness information of the subject under examination corresponding to the plurality of points, and the boundary display unit 322 can connect and show a plurality of coordinate positions of the target region plane by calculating the coordinate positions of the plurality of points mapped back to the target region plane, which is the real-time boundary. In some non-limiting embodiments, as many points as possible can be selected on the border of the mapping region 304 to acquire as many coordinate positions of the target region plane as possible, and thus a real-time boundary that is as accurate as possible can be acquired.

Specifically, the thickness information 308 of the subject under examination may be acquired by the camera unit, for example, determined by a 3D point cloud map acquired by the camera unit.

As the mouse moves, the position of the temporary end point changes, and the size of the reference region changes, while the real-time boundary is updated according to the movement of the mouse.

Figure 7:
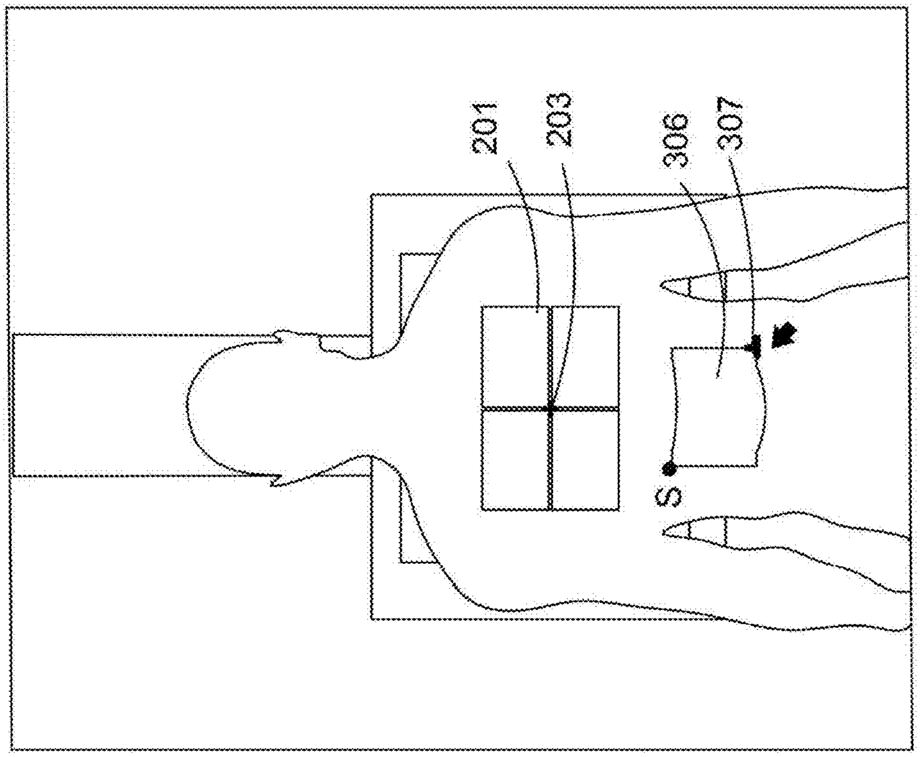
FIG. 7 is a schematic diagram of a third embodiment for determining a target region according to FIG. 5.

FIG. 7 is a schematic diagram of a third embodiment for determining a target region according to FIG. 5. As shown in FIG. 7, on the user interface, a real-time optical image of the subject under examination, the collimation region 201 and the center 203 of the collimation region on the optical image are displayed, and if the current collimation region is inaccurate and the user wants to re-define the collimation region, the foregoing can be configured to re-frame a new target region.

Specifically, in a process of re-framing a new target region, the control unit is able to use a dwell position of the input unit as the temporary end point during the movement of the input unit and based on the user-confirmed starting point S, and the control unit can determine the reference region based on the temporary end point, wherein the reference region is a non-rectangular real-time boundary 306, and the real-time boundary 306 is a real-time region boundary confirmed based on the thickness information of the subject under examination. Preferably, the user interface also shows a "cross", or "L", or "inverted T"-shaped indicator 307 at the temporary end point.

Figure 8:
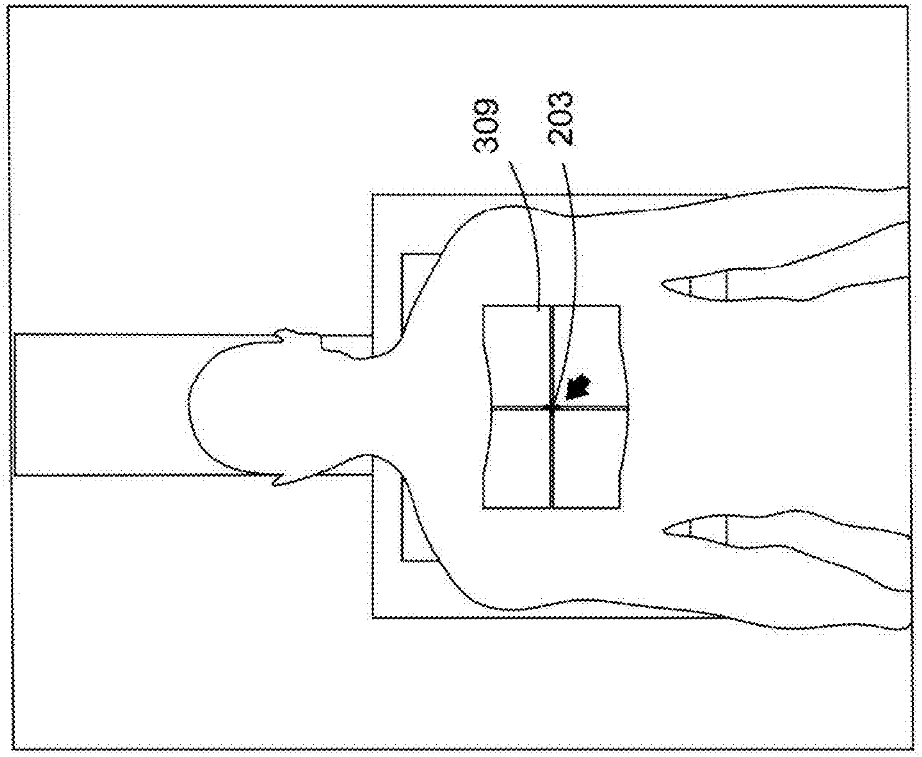
FIG. 8 is a schematic diagram of a fourth embodiment for determining a target region according to FIG. 5.

FIG. 8 is a schematic diagram of a fourth embodiment for determining a target region according to FIG. 5. As shown in FIG. 8, in the embodiment of changing the center of the collimation region, the control unit is able to indicate, after a user-determined center point is chosen or selected, the real-time boundary 309 corresponding to the reference region based on the temporary end point during the movement of the input unit.

Referring back to FIG. 6, in some embodiments, the camera unit is mounted on the side of the collimator, so that in order to enable the camera unit to be capable of being aligned with the center of the detector, the camera unit is fixed on the side of the collimator at a preset angle, and the center (i.e., the center of the X-ray source) of the collimator is aligned with the center of the detector. However, during actual use, the center of the optical image captured by the camera unit is offset from the center of the collimation region in the optical image, so that calibration needs to be performed thereon. The calibration may be performed by calculating the offset between the center of the optical image and the center of the collimation region.

Specifically, the control unit can calculate an offset between the center of the collimation region on the optical image and the center of the optical image based on the first angle between the camera unit and the vertical direction, the offset between the camera unit and the collimator, and the thickness information of the subject under examination, so as to calibrate the center of the collimation region. The offset between the camera unit and the collimator can be acquired by means of measuring when the camera unit is mounted. In some embodiments, when the collimator or the X-ray source is aligned at a preset second angle with the subject under examination or the detector, the control unit can calculate the offset between the center of the collimation region on the optical image and the center of the optical image based on the first angle, the second angle, the offset between the camera unit and the collimator, and the thickness information of the subject under examination.

Figure 9:
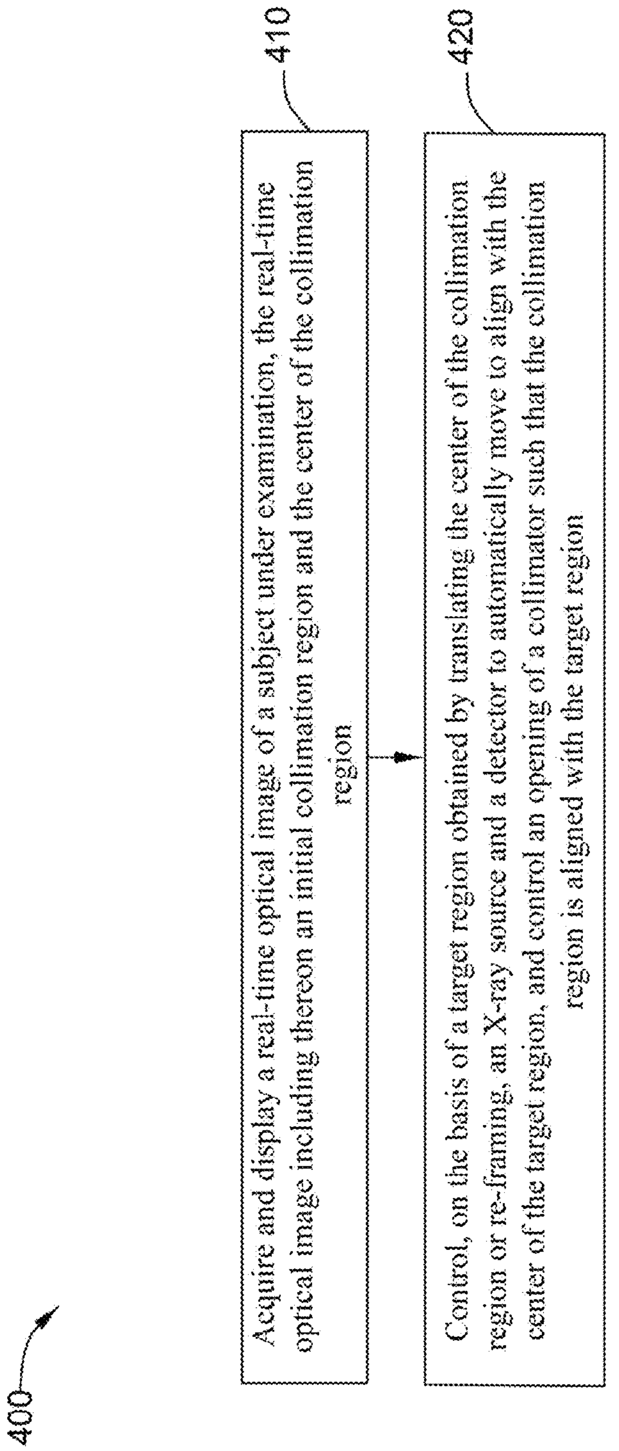
FIG. 9 is a flowchart of an X-ray imaging method according to some embodiments of the present invention.

FIG. 9 illustrates a flowchart of an X-ray imaging method 400 of some embodiments of the present invention. As shown in FIG. 9, the X-ray imaging method 400 includes step 410 and step 420.

In step 410, a real-time optical image of a subject under examination is acquired and displayed, and the real-time optical image includes thereon an initial collimation region and the center of the collimation region.

Specifically, a real-time optical image of the subject under examination can be acquired by the camera unit mounted in the scan room and transmitted to the display unit to display the real-time optical image on the display unit.

Specifically, the initial collimation region may be a region of interest identified based on information about the subject under examination, for example, based on information about the age of the subject, capture site, possible disease type, etc., and an X-ray source and a detector can be aligned with the center of the region of interest based on the region of interest, while an opening range of a collimator can also be adjusted based on the region of interest such that the collimation region can be aligned with the region of interest.

In step 420, the X-ray source and the detector are controlled, based on a target region obtained by changing the position of the center of the collimation region or re-framing, to automatically move to be aligned with the center of the target region, and an opening of the collimator is controlled such that the collimation region is aligned with the target region.

Specifically, re-framing the target region includes determining a valid starting point and determining a valid end point, and, after determining the starting point and before determining the end point, displaying a reference region formed by the starting point and a temporary end point in real time. Specifically, upon receiving a valid starting point, a real-time reference region is calculated and displayed based on the movement of an input unit, and upon receiving a valid end point input, the target region is acquired.

Determining a valid starting point includes determining, based on a received first press position and when the first press position is within the range of the optical image, that the first press position is a valid starting point. Of course, determining a valid starting point may include determining the first press position as a valid starting point when the first press position is within the outline range of the subject under examination. Of course, determining a valid starting point may include determining the first press position as a valid starting point when the first press position is within a preset distance from the outline boundary of the subject under examination.

In some aspects of the embodiment, determining the end point includes determining, based on a second press position and when the second press position has a preset distance from the first press position, the second press position as a valid end point. Of course, determining the end point may include determining the second press position as a valid end point when the second press position is to the lower right of the first press position.

In some other aspects of the embodiment, determining the end point includes determining, based on a first release position and when the first release position has a preset distance from the first press position, the first release position as a valid end point. Of course, determining the end point may include determining the first release position as a valid end point when the first release position is to the lower right of the first press position.

In some aspects of the embodiment, the real-time display of the reference region formed by the starting point and the temporary end point includes a rectangular reference region formed by acquiring the coordinate position of the current input unit dwell position and connecting the starting point and the temporary end point.

In some aspects of the embodiment, the real-time display of the reference region formed by the starting point and the temporary end point includes acquiring the coordinate position of the current dwell position of the input unit and acquiring a real-time boundary of the target region based on thickness information of the subject under examination.

Figure 10:
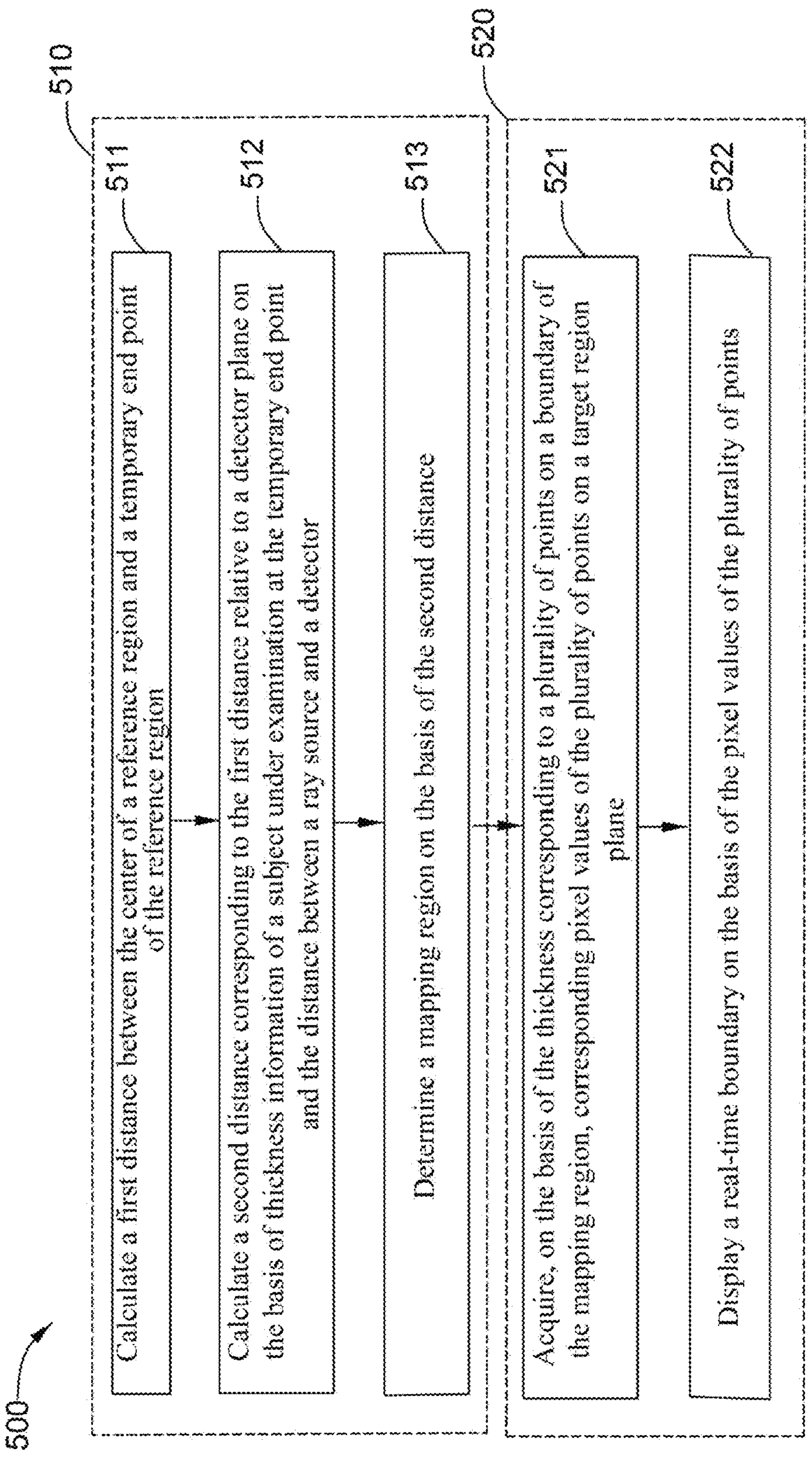
FIG. 10 is a flowchart of acquiring a real-time boundary of a reference region according to some embodiments of the present invention.

FIG. 10 illustrates a flowchart of a method 500 for acquiring a real-time boundary of a reference region in some embodiments of the present invention. As shown in FIG. 10, the method 500 for acquiring a real-time boundary of a reference region includes step 510 and step 520.

In step 510, a corresponding mapping region when a reference region is mapped to a detector plane is acquired.

In step 520, the real-time boundary is calculated based on the mapping region and thickness information of a subject under examination and displayed.

Specifically, step 510 includes step 511, step 512, and step 513.

In step 511, a first distance between the center of the reference region and a temporary end point of the reference region is calculated.

In step 512, a second distance corresponding to the first distance relative to the detector plane is calculated based on the thickness information of the subject under examination at the temporary end point and the distance between an X-ray source and a detector.

Specifically, a camera unit is mounted on a side of a collimator, and there is a fixed first angle between the camera unit and the side of the collimator, a second calculation unit being configured to acquire, based on the first angle and the thickness information of the subject under examination, the distance SOD between the X-ray source and the subject under examination, and calculate, based on the ratio between the distance SOD and the distance SID, the second distance corresponding to the first distance relative to the detector plane.

In step 513, the mapping region is determined based on the second distance.

Specifically, step 520 includes step 521 and step 522.

In step 521, based on position coordinates of a plurality of points on a boundary of the mapping region and the thickness of the subject under examination corresponding to the position, position coordinates of boundary points corresponding to the plurality of points in a target region plane are acquired.

In step 522, the real-time boundary is connected and displayed based on the position coordinates of the boundary points.

For the X-ray imaging system and the X-ray imaging method in some embodiments of the present invention, firstly, a real-time optical image of the subject under examination acquired by the camera is transmitted and displayed on the display unit, and the real-time optical image can be viewed in the control room, and the user can adjust the collimation region based on the real-time optical image, and the control unit can automatically control the X-ray source and the detector to move to the center of the target region based on the adjusted target region, and then automatically adjust the shutters of the collimator so as to adjust the range of the opening of the collimator to align the collimation region with the target region, so that the user can adjust and control the exposure assembly from within the control room. Secondly, the target region can be acquired by means of changing the position of the center of the collimation region or re-framing, which are easy operations. Furthermore, during the re-framing process, the user interface can display a reference target region in real time to show the user the possible range of the target region until the user confirms a valid end point, which is the final target region. Finally, in the process of adjusting the target region, a real-time boundary of the target region or the reference region can be displayed in real time, and the real-time boundary can be acquired based on the thickness information of the subject under examination, which can provide the user an actual boundary corresponding to the target region.

The present invention may further provide a non-transitory computer-readable storage medium for storing an instruction set and/or a computer program. When executed by a computer, the instruction set and/or computer program causes the computer to perform the image processing distribution method. The computer executing the instruction set and/or computer program may be a computer of a medical imaging system, or may be other apparatuses/modules of the medical imaging system. In one embodiment, the instruction set and/or computer program may be programmed into a processor/control apparatus of the computer.

Specifically, when executed by the computer, the instruction set and/or computer program causes the computer to:

acquire and display a real-time optical image of the subject under examination, the real-time optical image including thereon an initial collimation region and the center of the collimation region; and control, based on a target region obtained by changing the center of the collimation region or re-framing, the X-ray source and the detector to automatically move to be aligned with the center of the target region, and control the opening of the collimator such that the collimation region is aligned with the target region.

The instructions described above may be combined into one instruction for execution, and any of the instructions may also be split into a plurality of instructions for execution. Moreover, the present invention is not limited to the instruction execution order described above.

Exemplary embodiments of the present invention provide an X-ray imaging system. The X-ray imaging system includes a camera unit, a display unit, an input unit, an exposure assembly, and a control unit. The camera unit is configured to acquire a real-time optical image of the subject under examination. The display unit includes a user interface. The user interface is configured to display the real-time optical image, and the real-time optical image further includes thereon an initial collimation region and the center of the collimation region. The input unit is configured to receive a user operation, and to form a target region by translating the center of the collimation region or re-framing a region on the user interface. The exposure assembly includes an X-ray source, a detector, and a collimator. The collimator has an opening so as to be configured to display the collimation region on the subject under examination. The control unit is configured to control, based on the target region, automatic movement of the X-ray source and the detector to align with the center of the target region, and control the opening of the collimator such that the collimation region is aligned with the target region.

Specifically, the control unit is configured to calculate the center position, length, and width of the target region, and to move, according to the center position, the X-ray source and the detector to align with the center of the target region, and to adjust the opening of the collimator according to the length and width.

Specifically, the control unit is capable of: after receiving a valid starting point input, calculating, based on the movement of the input unit, a real-time reference region and displaying the same on the display unit, and, after receiving a valid end point input, acquiring the target region.

Specifically, the control unit is configured to receive a first press position inputted by the input unit, and determine the first press position as a valid starting point when the first press position is within the range of the optical image.

Specifically, the control unit is configured to receive a second press position inputted by the input unit, and determine the second press position as a valid end point when the second press position has a preset distance from the first press position.

Specifically, the control unit is configured to receive a first release position inputted by the input unit, and determine the first release position as a valid end point when the first release position has a preset distance from the first press position.

Specifically, the display unit further includes a confirmation option thereon, so as to be configured to confirm the range of the target region.

Specifically, the real-time reference region is rectangular.

Specifically, the real-time reference region is a non-rectangular real-time boundary.

Specifically, the control unit further includes a first unit and a second unit. The first unit is configured to acquire a mapping region corresponding to the reference region mapped to a detector plane. The second unit is configured to calculate, based on the mapping region and thickness information of the subject under examination, the real-time boundary and display the same on a target region plane.

Specifically, the first unit includes a first calculation unit, a second calculation unit, and a first mapping unit. The first calculation unit is configured to calculate a first distance between the center of the reference region and a temporary end point of the reference region. The second calculation unit is configured to calculate a second distance corresponding to the first distance relative to the detector plane based on the thickness information of the subject under examination at the temporary end point and the distance SID between the X-ray source and the detector. The first mapping unit is configured to determine the mapping region based on the second distance.

Specifically, a camera unit is mounted on a side of the collimator, and there is a fixed first angle between the camera unit and the side of the collimator, the second calculation unit being configured to acquire, based on the first angle and the thickness information of the subject under examination, the distance SOD between the X-ray source and the subject under examination, and calculate, based on the ratio between the distance SOD and the distance SID, the second distance corresponding to the first distance relative to the detector plane.

Specifically, the second unit includes a second mapping unit and a boundary display unit. The second mapping unit is configured to acquire, based on position coordinates of a plurality of points on a boundary of the mapping region and the thickness of the subject under examination corresponding to the position, position coordinates of boundary points corresponding to the plurality of points in the target region plane. The boundary display unit is configured to connect and display the real-time boundary based on the position coordinates of the boundary points.

Specifically, the camera unit is mounted on the side of the collimator, and there is a fixed first angle between the camera and the side of the collimator, the control unit being capable of calculating an offset between the center of the collimation region on the optical image and the center of the optical image based on the first angle, an offset between the camera unit and the collimator, and the thickness information of the subject under examination to calibrate the center of the collimation region.

Exemplary embodiments of the present invention provide an X-ray imaging system. The X-ray imaging system comprises a display unit having a graphical user interface, the graphical user interface being capable of displaying a real-time optical image of the subject under examination, the real-time optical image further comprising thereon an initial collimation region and the center of the collimation region, and, during movement of an input unit, displaying in real time a reference region of a current position on the optical image based on a starting point inputted by the input unit, and, after an input of an end point is determined, the collimation region being capable of automatically aligning a target region framed by the starting point and the end point.

Specifically, the position of the temporary end point further includes a position indicator.

Specifically, the reference region is a non-rectangular real-time boundary.

Specifically, the changing the position of the center of the collimation region includes translating the center of the collimation region or reselecting the position of the center of the collimation region.

Exemplary embodiments of the present invention further provide an X-ray imaging method, the method including acquiring and displaying a real-time optical image of a subject under examination, the real-time optical image including thereon an initial collimation region and the center of the collimation region, controlling, based on a target region obtained by changing the center of the center of the collimation region or re-framing, an X-ray source and a detector to automatically move to be aligned with the center of the target region, and controlling an opening of a collimator such that the collimation region is aligned with the target region.

Specifically, the re-framing includes: after receiving a starting point input, calculating, based on the movement of an input unit, a real-time reference region and displaying the same, and after receiving an end point input, acquiring the target region.

Specifically, the displaying a real-time reference region includes displaying a real-time boundary of the reference region.

Specifically, the displaying a real-time boundary of the reference region includes: acquiring a mapping region corresponding to the reference region mapped to a detector plane; and calculating, based on the mapping region and thickness information of the subject under examination, the real-time boundary and displaying the same on a target region plane.

Specifically, the acquiring a mapping region includes: calculating a first distance between the center of the reference region and a temporary end point of the reference region; calculating a second distance corresponding to the first distance relative to the detector plane based on the thickness information of the subject under examination at the temporary end point and the distance SID between the X-ray source and the detector; and being configured to determine the mapping region based on the second distance.

Specifically, the calculating the real-time boundary and displaying the same on a target region plane includes: acquiring, based on position coordinates of a plurality of points on a boundary of the mapping region and the thickness of the subject under examination corresponding to the position, position coordinates of boundary points corresponding to the plurality of points in the target region plane; and connecting and displaying the real-time boundary based on the position coordinates of the boundary points.

As used herein, the term "computer" may include any processor-based or microprocessor-based system, including a system using a microcontroller, a reduced instruction set computer (RISC), an application-specific integrated circuit (ASIC), a logic circuit, and any other circuit or processor capable of performing the functions described herein. The examples above are exemplary and are not intended to limit the definition and/or meaning of the term "computer" in any way.

The instruction set may include various commands used to instruct the computer serving as a processing machine or the processor to perform specific operations, for example, methods and processes of various embodiments. The instruction set may be in the form of a software program that may form part of one or more tangible, non-transitory computer readable media. The software may be in various forms of, for example, system software or application software. Furthermore, the software may be in the form of a standalone program or a collection of modules, a program module within a larger program, or part of a program module. The software may also include modular programming in the form of object-oriented programming. Processing of input data by the processing machine may be in response to an operator command, or in response to a previous processing result, or in response to a request made by another processing machine.

As used herein, the term "computer" may include any processor-based or microprocessor-based system, including a system using a microcontroller, a reduced instruction set computer (RISC), an application-specific integrated circuit (ASIC), a logic circuit, and any other circuit or processor capable of performing the functions described herein. The examples above are exemplary and are not intended to limit the definition and/or meaning of the term "computer" in any way.

Some exemplary embodiments have been described above; however, it should be understood that various modifications may be made. For example, suitable results can be achieved if the described techniques are performed in a different order and/or if components in the described systems, architectures, devices, or circuits are combined in different ways and/or replaced or supplemented by additional components or equivalents thereof. Accordingly, other implementations also fall within the scope of protection of the claims.

The invention claimed is:

1. An X-ray imaging system, comprising:

an exposure assembly including an X-ray source, a detector, and a collimator, the collimator having an opening for controlling a collimation region;

a camera unit aligned with the detector for acquiring a real-time optical image of a subject under examination, the real-time optical image including a center of the collimation region;

a display unit operably connected to the camera unit, the display unit including a user interface configured to display the real-time optical image;

an input unit operably connected to the display unit, the input unit configured to receive an operation of a user and form a target region on the user interface by changing a position of the center of the collimation region or re-framing a region of the collimation region; and a control unit operably connected to the exposure assembly, the control unit configured to control, based on the target region, automatic movement of the X-ray source and the detector to align with a center of the target region, and control the opening of the collimator such that the collimation region is aligned with the target region;

wherein the control unit is configured to receive a first press position inputted by the input unit and determine the first press position as a valid starting point when the first press position is within a range of the real-time optical image, and wherein the control unit is configured to receive a second press position inputted by the input unit, and determine the second press position as a valid end point when the second press position or the first release position has a preset distance from the first press position.

2. The X-ray imaging system of claim 1, wherein the control unit calculates a center position, a length, and a width of the target region, and moves, according to the center position, the X-ray source and the detector to align with the center of the target region, and adjusts the opening of the collimator according to the length and the width.

3. The X-ray imaging system of claim 1, wherein the control unit, after receiving a valid starting point input, calculates, calculates movement of the input unit, a reference region and displaying the same on the display unit, and, after receiving a valid end point input, acquires the target region.

4. The X-ray imaging system of claim 3, wherein the display unit includes a confirmation option thereon to confirm a range of the target region.

5. The X-ray imaging system of claim 3, wherein the reference region is rectangular.

6. The X-ray imaging system of claim 3, wherein the reference region is a non-rectangular real-time boundary.

7. The X-ray imaging system of claim 6, wherein the control unit includes:

a first unit configured to acquire a mapping region corresponding to the reference region mapped to a detector plane; and a second unit configured to calculate, based on the mapping region and thickness information of the subject under examination, the real-time boundary and display the same on a target region plane.

8. The X-ray imaging system of claim 7, wherein the first unit includes:

a first calculation unit configured to calculate a first distance between the center of the reference region and a temporary end point of the reference region;

a second calculation unit configured to calculate a second distance corresponding to the first distance relative to the detector plane based on the thickness information of the subject under examination at the temporary end point and a distance between the X-ray source and the detector; and a first mapping unit configured to determine the mapping region based on the second distance.

9. The X-ray imaging system of claim 8, wherein the camera unit is mounted on a side of the collimator, and there is a fixed first angle between the camera unit and the side of the collimator, the second calculation unit being configured to acquire, based on the fixed first angle and thickness information of the subject under examination, a distance between the X-ray source and the subject under examination, and calculate, based on the ratio between the distance between the X-ray source and the subject under examination and the distance between the X-ray source and the detector, the second distance corresponding to the first distance relative to the detector plane.

10. The X-ray imaging system of claim 8, wherein the second unit includes:

a second mapping unit configured to acquire based on position coordinates of a plurality of points on a boundary of the mapping region and the thickness of the subject under examination corresponding to the position, position coordinates of boundary points corresponding to the plurality of points in the target region plane; and a boundary display unit configured to connect and display the real-time boundary based on the position coordinates of the boundary points.

11. An X-ray imaging system, comprising:

an exposure assembly including an X-ray source, a detector, and a collimator, the collimator having an opening for controlling a collimation region;

a camera unit aligned with the detector for acquiring a real-time optical image of a subject under examination, the real-time optical image including a center of the collimation region;

a display unit operably connected to the camera unit, the display unit including a user interface configured to display the real-time optical image;

an input unit operably connected to the display unit, the input unit configured to receive an operation of a user and form a target region on the user interface by changing a position of the center of the collimation region or re-framing a region of the collimation region; and a control unit operably connected to the exposure assembly, the control unit configured to control, based on the target region, automatic movement of the X-ray source and the detector to align with a center of the target region, and control the opening of the collimator such that the collimation region is aligned with the target region, wherein the camera unit is mounted on a side of the collimator, and there is a fixed first angle between the camera and the side of the collimator, the control unit being capable of calculating an offset between the center of the collimation region on the real-time optical image and the center of the real-time optical image based on the fixed first angle, an offset between the camera unit and the collimator, and thickness information of the subject under examination to calibrate the center of the collimation region.

12. An X-ray imaging system, comprising:

an exposure assembly including an X-ray source, a detector, and a collimator, the collimator having an opening for controlling a collimation region;

a camera unit aligned with the detector for acquiring a real-time optical image of a subject under examination, the real-time optical image including a center of the collimation region;

a display unit operably connected to the camera unit, the display unit including a user interface configured to display the real-time optical image;

an input unit operably connected to the display unit, the input unit configured to receive an operation of a user and form a target region on the user interface by changing a position of the center of the collimation region or re-framing a region of the collimation region; and a control unit operably connected to the exposure assembly, the control unit configured to control, based on the target region, automatic movement of the X-ray source and the detector to align with a center of the target region, and control the opening of the collimator such that the collimation region is aligned with the target region, wherein the input unit is configured to move, and wherein during movement of the input unit, the display unit displays in real time on the real-time optical image, based on a starting point inputted by the input unit, a reference region formed by a temporary end point, and, after an input of an end point is determined, the collimation region automatically aligns with the target region framed by the starting point and the end point.

13. The X-ray imaging system according to claim 12, wherein the position of the temporary end point further comprises a position indicator.

14. The X-ray imaging system according to claim 12, wherein the reference region is a non-rectangular real-time boundary.

* * * * *